United States Patent
Huang et al.

(10) Patent No.: US 6,440,658 B1
(45) Date of Patent: Aug. 27, 2002

(54) ASSAY METHOD FOR DETERMINING PRODUCT R'S EFFECT ON ADENOVIRUS INFECTION OF HELA CELLS

(75) Inventors: Wenlin Huang, Philadelphia, PA (US); Shalom Z. Hirschman, Riverdale, NY (US)

(73) Assignee: Advanced Viral Research, Yonkers, NY (US)

( * ) Notice: Subject to any disclaimer, the term of this patent is extended or adjusted under 35 U.S.C. 154(b) by 0 days.

(21) Appl. No.: 09/705,618

(22) Filed: Nov. 3, 2000

Related U.S. Application Data
(60) Provisional application No. 60/163,550, filed on Nov. 4, 1999.

(51) Int. Cl.[7] .............................. C12Q 1/70; C12Q 1/06
(52) U.S. Cl. ............................................. 435/5; 435/39
(58) Field of Search ........................................ 435/5, 39

(56) References Cited

PUBLICATIONS

References sited on p. 17 of the specification have been considered.*

\* cited by examiner

*Primary Examiner*—Hankyel T. Park
(74) *Attorney, Agent, or Firm*—Cohen, Pontani, Lieberman & Pavane

(57) ABSTRACT

An assay method for determining the effect of Product R on virus infection of Hela cells. The method comprising the following step: (1) dividing Hela cells into several groups, (2) treating one group with Product R prior to infecting the cells with a virus and treating another group with Product R after the cells being infected with the virus, and (3) determining the effects of Product R on virus infection by comparing the changes in the cell cycle, DNA fragmentation and p53 protein in cells undergone the different treatments in step (2).

12 Claims, 3 Drawing Sheets

ASSAY METHOD FOR DETERMINING PRODUCT R'S EFFECT ON ADENOVIRUS INFECTION OF HELA CELLS

RELATED APPLICATIONS

This application claims priority from U.S. Provisional Patent Application Ser. No. 60/163,550 which was filed on Nov. 4, 1999.

BACKGROUND OF THE INVENTION

1. Field of the Invention

The present invention relates to a biological assay method. Particularly, it pertains to a method for determining the effect of Product R on adenovirus infection of Hela cells.

2. Description of the Related Art

Product R is an antiviral agent useful for treating a wide range of viral infections, such as infections of human immunodeficiency virus (HIV), herpes simplex virus, adenovirus. It has become known that Product R is effective in stimulating the production of chemokines, including interferon-gamma, interleukin-6 and interleukin-1. Product R is described in detail in U.S. patent application Ser. No. 09/344,095, which is incorporated herein by reference in its entirety. However, the mechanism of Product R in treating human viral infections is yet to be fully understood. Improved methods for detecting and measuring Product R's existing or potential biological activities are thus desired. To applicant's knowledge, no one has heretofore taught or suggested any assay directing to measuring Product R's effect on adenovirus infection of Hela cells.

Significant progress has been made in unraveling the details of the molecular circuits that regulate the cell cycle engine, as well as of the surveillance mechanisms (checkpoints) that ensure that chromosome duplication and segregation take place only when appropriate. In mammalian cells, both DNA synthesis (passage through $G_1$ into $G_2$ phase) and re-entry into the cell cycle from $G_0$ depend on external growth factors and other agents that stimulate cell growth and division (mitogens). Late in $G_1$ cells responding to such external cues become committed to enter S phase, divide and complete the cell cycle. During this time they are refractory to extracellular signals that regulate growth. Cells that have entered this state are said to have passed the $G_1$ restriction point. The genomes of several DNA viruses encode proteins that are mitogenic because they subvert the normal mechanisms of restriction point control. Indeed, the functions of critical components of these cellular regulatory mechanisms has initially been deduced through the activity of such viral proteins.

The most unexpected result to emerge from these genetic studies is the difference between the 5V40 and polyomavirus early proteins needed for transformation. SV40LT is essential for induction of transformation, with sT being required for the expression of specific phenotypes in certain cell types. In contrast, polyomavirus LT is not sufficient for transformation, nor are the sequences encoding its C-terminal segment necessary. Rather, polyomavirus middle T antigen, an early protein that has no counterpart in the 5V40 genome, is necessary both to establish and maintain the transformed state.

Although the human pathogens HILV-1 and HIV-1 both have complex genomes that encode regulatory proteins, they belong to two distinct groups. HIV-1 is a member of the lentivirus group. Although HIV-1 is not known to transform cells that it infects, a relatively high incidence of an otherwise rare cancer, called Kaposi's sarcoma, is associated with AIDS. This type of tumors is thought to be associated with expression of the HIV regulatory protein Tat, an idea supported by the finding that mice transgenic for HIV Tat develop a disease analogous to Kaposi's sarcoma. The Tat protein has an RGD domain like that found on extracellular matrix proteins and thus may stimulate integrins on epithelial cells, causing inappropriate proliferation. HIV-1 encodes another protein, called Vpr, which prevents proliferation of infected cells by arresting them in the $G_2$ phase of the cell cycle. (1) This Vpr-mediated cell-cycle arrest has also been observed in several highly divergent simian immunodeficiency viruses, suggesting an important role for this protein in the virus life cycle. The expression of the viral genome is optimal in the G2 phase of the cell cycle, and Vpr increases viral production by delaying cells at the point of the cell cycle where the long terminal repeat (LTR) is more active.

Adenovirus is an ideal model for studying the interaction between cellular and viral genes in gene regulation. The cellular DNA-binding protein, E2F, was identified originally by its ability to bind to a specific recognition sequence in adenovirus E2 promoter. In addition, the viral protein, E1A has been shown to induce E2F-mediated DNA binding and transcriptional activities by releasing free E2F from inactive protein complexes. The significance of these findings was limited until it was observed that promoters of many cellular genes contain similar E2F-binding sites and that E2F is one of the important cellular transcription factors in regulating expression of some of these genes. Many of these genes are involved in cell cycle progression, particularly in DNA synthesis. Furthermore, several key regulators of the cell cycle, including the retinoblastoma protein (Rb) and related proteins p107 and p130, were found to form complexes with E2F, indicating the potential role of E2F in cell cycle progression. By its ability to bind to the Rb protein, E2F-1 was the first gene product identified among a family of E2F transcription factors. As an authentic transcription factor, E2F-1 contains a specific DNA-binding domain and a potent transactivation region. E2F-1 can form heterodimers with another E2F-like protein, DP-1, and have a synergistic effect on its transcription activity. The Rb-binding domain of E2F-1 overlaps its transcriptional activation region, suggesting a possible mechanism for Rb to regulate E2F-1 transcriptional activity. Indeed it has been shown that Rb suppresses transcriptional activation mediated by E2F-1 through the direct interaction between the two molecules. The inhibitory effects of Rb can be disrupted by its direct interaction with viral oncoproteins, such as E1A, an effect similar to that achieved by mutation or phosphorylation of the Rb protein. A noteworthy observation made during the original characterization of E2F-1 was that expression of this protein is cell cycle dependent, with a peak at the $G_1/s$ boundary. This finding is consistent with the hypothesis that E2F functions primarily at this period of time in the cell cycle and that E2F-1 mediated transcriptional activation may be one of the rate-limiting steps in cell proliferation. Indeed, deregulated expression of E2F-1 in Rat-2 fibroblasts was found to induce premature entry into S-phase, subsequently leading to apoptotic cell death.

Cyclin B is first synthesized during S phase, accumulates in complexes with $p34^{cdc2}$ as cells approach the $G_2$ to M transition, and is abruptly degraded during mitosis. Phosphorylation of $p34^{cdc2}$ on threonine-161 may stabilize its binding to cyclin B and is required for the subsequent activation of the enzyme. Other phosphorylations at threonine14 and tyrosine-15 within the $p34^{cdc2}$ ATP-binding site maintain the kinase in an inactive form throughout S and $G_2$.

Removal of the inhibitory phosphates from cyclin B-associated p34$^{cdc2}$ at the G$_2$/M transition activates the p34$^{cdc2}$ kinase and triggers entry into mitosis. Conversely, exit from mitosis depends upon the abrupt ubiquitin-mediated degradation of cyclin B during anaphase, resulting in the release of p34$^{cdc2}$ as an inactive monomer. Checkpoint controls impinging upon the kinases and phosphatases that regulate p34$^{cdc2}$ activity ensure that S phase ends before mitosis begins.(1)

Progression of eukaryotic cells through the cell cycle is governed by the sequential formation, activation, and subsequent inactivation of a series of cyclin-dependent kinase (Cdk) complexes. The mechanisms underlying the expression of cyclins and the activation of the different cyclin-Cdk complexes needed for progression through the successive cell cycle transitions are now fairly well understood. In addition to positive regulation by the activation of cyclin-Cdk complexes, negative regulation of the cell cycle occurs at checkpoints, which are the transitions where feedback mechanisms operate to prevent premature entry of the cell into the next phase of the cycle prior to completion of the necessary macromolecular events. Among the best-documented checkpoints are those that monitor the completion of DNA synthesis and the formation of a functional spindle, acting at the G$_2$ to M transition and the exit from mitosis, respectively (2)

In at least some systems, unreplicated DNA blocks activation of the cyclin B-Cdc2 complex by preventing the dephosphorylation of Tyr-15 (and Thr-14) in Cdc2, which is required for its activation and the triggering of the G2 to M transition (Enoch and Nurse, 1991). This feedback requires several gene products and apparently results in the activation of Wee1-Mik1-related related protein kinases, which phosphorylate these sites in Cdc2. There are also checkpoints earlier in the cycle that control entry into S phase; while these are dependent on the integrity of the genome and nutrient/growth factor status, the molecular mechanisms of these checkpoints are not well understood (2). The cell cycle may have clinical implications, since the cell cycle components that have been implicated in viral infection might provide new targets for therapeutic strategies. It might be possible, for example, to inhibit viral DNA replication or transcription by blocking the activation of the cell cycle by cyclin D1 or other cyclins, or by mimicking the effects of the inhibitors (4).

One example of this is the protein encoded by the p53 tumor suppressor gene, which apparently inhibits cell growth by inducing the synthesis of a protein that acts to arrest the cell cycle (3). The p53 protein has been shown to function as a transcription factor that positively and negatively regulates a set of cellular genes, some of which participate in cell cycle regulation and others in the commitment to express differentiated functions. The isolation of these genes and the determination of the pathway by which p53 regulates them is one of the major goals of the laboratory.

In human cancers, p53 mutations are the single most common genetic alteration detected to date. Missense mutations producing faulty p53 proteins that contribute to abnormal cell proliferation in tumors are most common in carcinomas. These altered genes have been cloned and isolated and shown to contribute to transformation of cells in culture as well as tumorigenesis in animals. Transgenic animals, with no p53 gene or missense mutations in these genes, inherit predispositions to cancers. Similarly, humans with germline p53 mutations are part of families with high incidences of cancer. The transgenic mice with p53 mutations are therefore excellent model systems for studying the evolution of the origins of cancers as well as virus-induced programmed cell death.

In contrast to carcinomas, sarcomas in humans rarely have p53 mutations that produce faulty proteins. Some sarcomas display amplification of a second gene, called mdm-2, that produces a protein that binds to p53 and eliminates its ability to function as a transcriptional activator. The mdm-2 gene product acts like the oncogenes of the DNA tumor viruses. The mdm2 gene contains a p53 responsive element, and the level of mdm2 mRNA is therefore regulated by p53. This results in an autoregulatory loop, in which p53 controls the level of mdm-2 message and mdm-2 controls the activity of p53.

In viral infections, p53 has garnered much attention, because p53-dependent apoptosis contributes to the development of human disease associated with virus infection. The protein coded for by p53 has been shown to stimulate the production of another protein, and the second protein inhibits key enzymes needed to drive cells through the cell cycle and into mitosis. It might be possible, therefore, to design drugs that block virus replication by mimicking the inhibitory effects of the p53-induced protein on cell cycle enzymes. Passage of cells through the cycle depends on the activity of enzymes known as "cyclin-dependent kinases" (Cdks) because they become active only when they associate with protein partners called cyclins (5).

Human Ad may also encode proteins that function as inducers of apoptosis at later stages of infection. Cytotoxicity of Ad was originally believed to originate from the E1A protein, which induces accumulation of p53 and p53-dependent apoptosis. However, Ad has also been shown to induce apoptosis in the absence of p53 (7, 8) and this activity is dependent on one or more E4 gene products (9). The induction of both p53-dependent and p53 independent apoptosis may explain the need for two E1B proteins, E1B-55K, which prevents p53-mediated cell death, and E1b-19K, which blocks all forms of apoptosis. The identity of the E4 protein(s) involved and the mechanism of cell death are under investigation. In addition, an E3 product has recently been implicated in Ad-induced cell death (10). The E3-1 1.6K product, termed the Ad death protein (ADP), is only expressed in large amounts during the very late stages of infection, and it is still unclear whether cell death is due to apoptosis (6).

The small DNA tumor viruses, SV40, the human adenoviruses, and the human papilloma viruses induce tumors and transform cells in culture by encoding and expressing one or more oncogenes that alter the replication cycle of the host cell. These oncogene products, the SV40 large T antigen, the adenovirus E1A and E1B proteins, and the papilloma virus E6 and E7 proteins, each interact with and inactivate the products of the tumor suppressor genes, Rb and p53. These latter genes have been found to encode proteins that act as checkpoints in the cell cycle by either negatively regulating cell division or initiating apoptosis or programmed cell death. Thus, by binding to and inactivating the p53 protein, the DNA tumor viruses may alter normal cells and initiate tumor growth.

SUMMARY OF THE INVENTION

One object of the present invention is to provide a method for determining the effects of Product R on adenovirus infection of Hela cells. The method involves (1) treating Hela cells with Product R before and after the cells are infected with adenovirus and (2) then determining the changes of a number of biological criteria reflecting the degree of adenovirus infection of the cells, including changes in the number of the cells in various cell cycle phases, in the number of cells that have undergone apoptotic cell death, in the degree of cell DNA fragmentation, and in the amount of the p53 protein.

Using this method, applicants have determined that Product R may block virus infection of human cells by interfering with DNA replication, reflecting a higher percentage of G2 cells and a reduced number of cells in apoptosis when the cells are treated with Product R prior to adenovirus infection. Therefore, it is another object of the present invention to provide a method to study Product R's existing and potential biological activities.

Other objects and features of the present invention will become apparent from the following detailed description considered in conjunction with the accompanying drawings. It is to be understood, however, that the description and drawings are provided solely for purposes of illustration and not as a definition of the limits of the invention, for which reference should be made to the claims.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
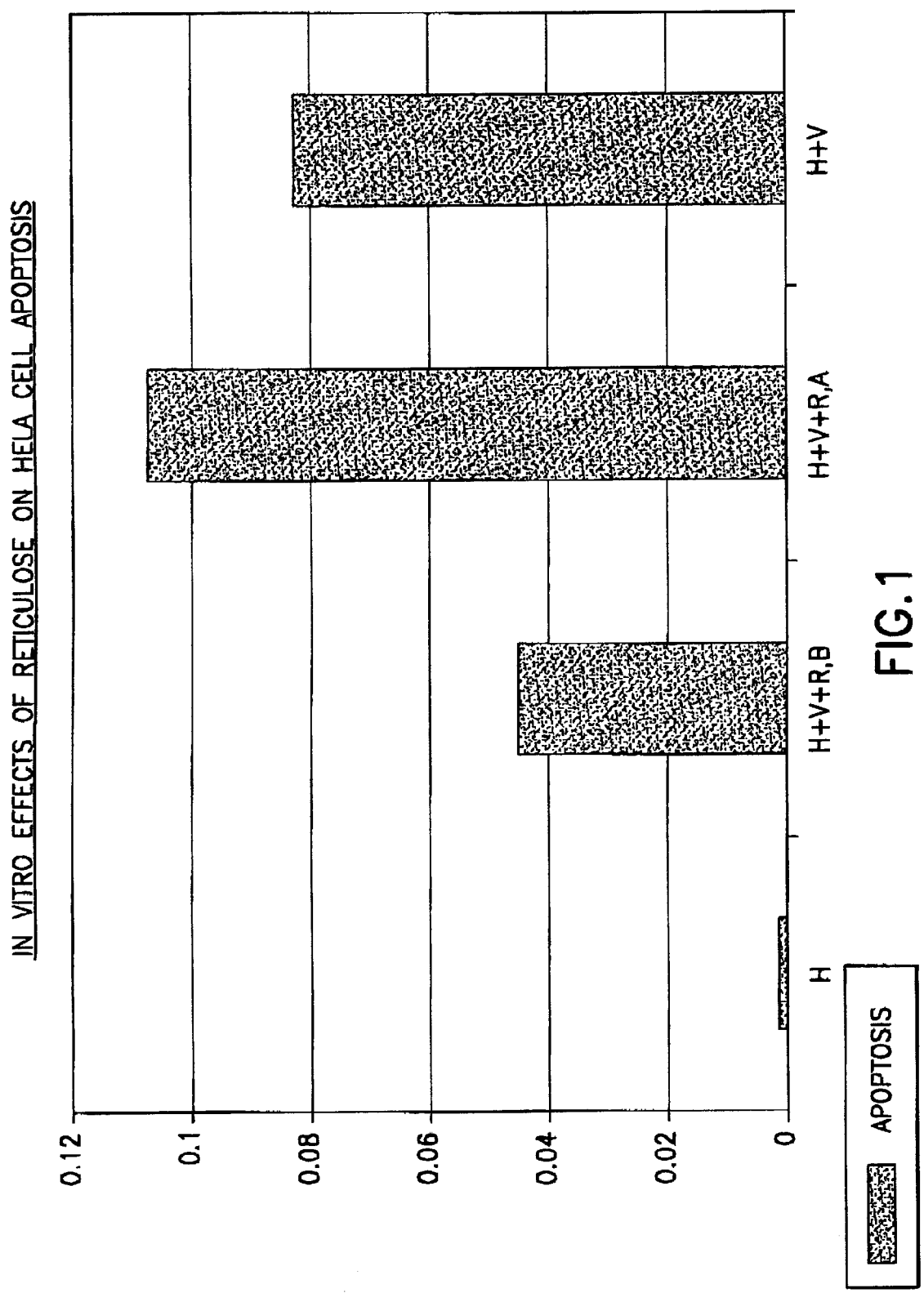
FIG. 1 depicts in vitro experimental data obtained in an assay conducted according to the present invention, showing the effects of Product R on apoptosis of Hela cells.

A specific embodiment of the present invention is described herein in detail, which comprising the following steps:

(1) Cell Culture

Hela cells were grown at 37° C. in 5% $CO_2$ in Dulbecco's modified Eagles medium (DMEM) supplemented with 5% calf serum, 5% fetal calf serum and 1 mM glutamine. H9 cells were cultured at 37° C. in 5% $CO_2$ in RMPI 1640 medium containing 10% fetal calf serum.

(2) Adenovirus preparation

Adenovirus was harvested after infection of 293 cells for 24 hours. The cells are washed twice with PBS, and the supernatants are discarded. The pellets are frozen on dry ice and lyophilized in a 37° C. water bath for 3 cycles. The lyophilized cells are centrifuged at 8,000×g for 30 mm. The supernatant, which contains the virus, is applied to a CsCl gradient and ultracentrifuged at 45,000×g for 18 hours. The virus band is collected and dialyzed in TE buffer for at least 4 hours at 4° C. The yield of adenovirus was determined by a plaque assay on Hela cells.

(3) Product R

Product R can be obtained from Advanced Viral Research Corporation (Yonkers, N.Y.), and is fully described in U.S. patent application Ser. No. 09/344,095, which is incorporated herein by reference in its entirety.

(4) Adenovirus infection and Product R treatment

Five groups of HeLa cells are seeded onto 150 mm plates and allowed to grow to confluence. Group 1 is treated with neither Product R nor virus. Groups 2 and 3 are pretreated with 100% Product R for one hour at 37° C. in 5% $CO_2$, after which Group 3 is infected with 20 pfu/cell of adenovirus type 5. Groups 4 and 5 are infected with 20 pfu/cell of adenovirus type 5 for one hour, after which Group 4 is treated with 100% Product R for one hour at 37° C. in 5% $CO_2$. The cells in all groups are subsequently cultured for 14 hours in DMEM supplemented with 5% fetal calif serum and 5% calf serum.

(5) DNA fragmentation analysis

Cells ($5\times10^5$) are lysed in 1 ml 10 mM Tris (pH 7.9), 5 mM EDTA, 10 mM NaCl, 0.5% SDS, 1 mg/ml of pronase for 2 hours at 37° C. Sufficient 5 M NaCl is added to adjust the NaCl concentration to 1 M. High molecular weight DNA is removed by centrifugation at 57,000×g for 20 mm at 4° C. The supernatant is extracted with phenol and chloroform, and the low molecular weight DNA is recovered by ethanol precipitation. The DNA is treated with RNase A (20 g/ml) and analyzed by electrophoresis on a 1.25% agarose gel.

(6) Flow cytometry analysis

The five groups of Hela cells are treated as described in paragraph (3). Aliquots of $10^6$ cells were trypsinized, fixed in 70% cold methanol, and stained with propidium iodide. Flow cytometry analysis was performed on a FAXS can, using a Cell Quest analysis program.

(7) Western blotting Lysates from $5\times10^5$ were boiled in sodium dodecyl sulfate (SDS) loading buffer and applied to a 10% polyacrylamide gel. Following electrophoresis, the proteins were transferred to an Immobilon-P membrane. The membranes were washed and incubated with a mouse monoclonal antibody to human p53 protein. Following another wash, the membranes were incubated with goat anti-mouse IgG conjugated with alkaline phosphatase.

As shown in FIG. 1, which depicts the results obtained from a particular experiment embodying the present invention, Hela cells treated with virus and/or Product R were also assayed for the percentage of cells that had undergone apoptotic cell death. While virtually none of the Hela cells the control group had undergone apoptosis, infection with adenovirus induced apoptosis in about 8% of the cells. Treatment of adenovirus-infected cells with Product R increased the number of apoptotic cells to 11%. In contrast, pretreatment of Hela cells with Product R, followed by infection with adenovirus, reduced the number of cells in apoptosis to 4%

Figure 2:
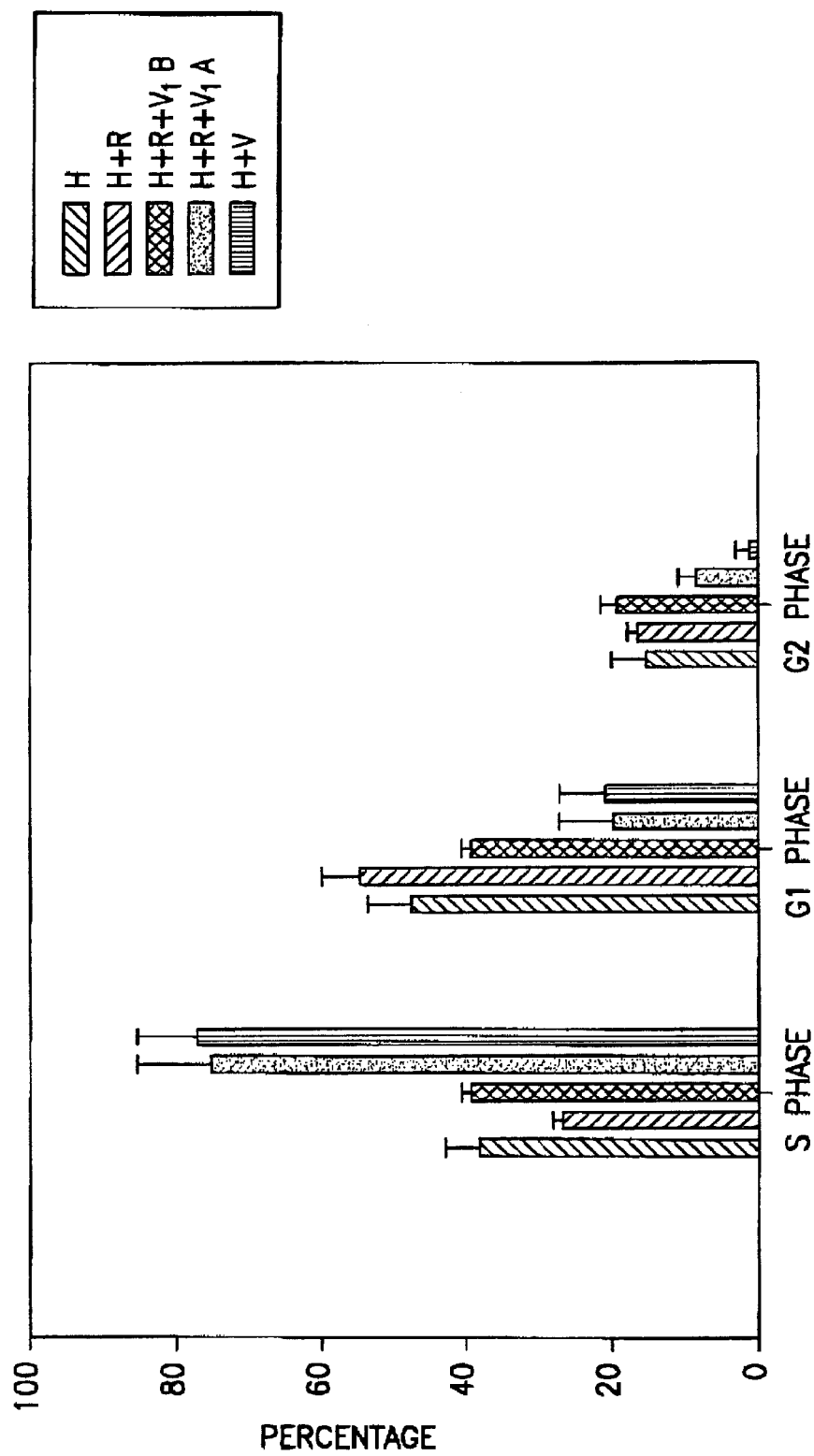
FIG. 2 depicts in vitro experimental data obtained in another assay conducted according to the present invention, showing the effects of Product R on cell cycle of Hela cells.

Referring now to FIG. 2, the flow cytometry analysis of the resultant cells shows that viral infection alone significantly increased the number of cells in S phase and significantly decreases the number of cells in both G1 and G2. Treatment of Hela cells with Product R alone decreases the number of cells in S phase and increases the number of cells in G1 phase, hut has no effect on the number of cells in G2 phase. When Product R treated cells are infected with virus, the percentages of cells in S and G1 are about the same as those observed in virally-infected cells, whereas the percentage of cells in G2 is significantly higher. In contrast, when virally-infected cells are treated with Product R, the cell cycle phases resembles those of untreated virally-infected HeLa cells.

Figure 3:
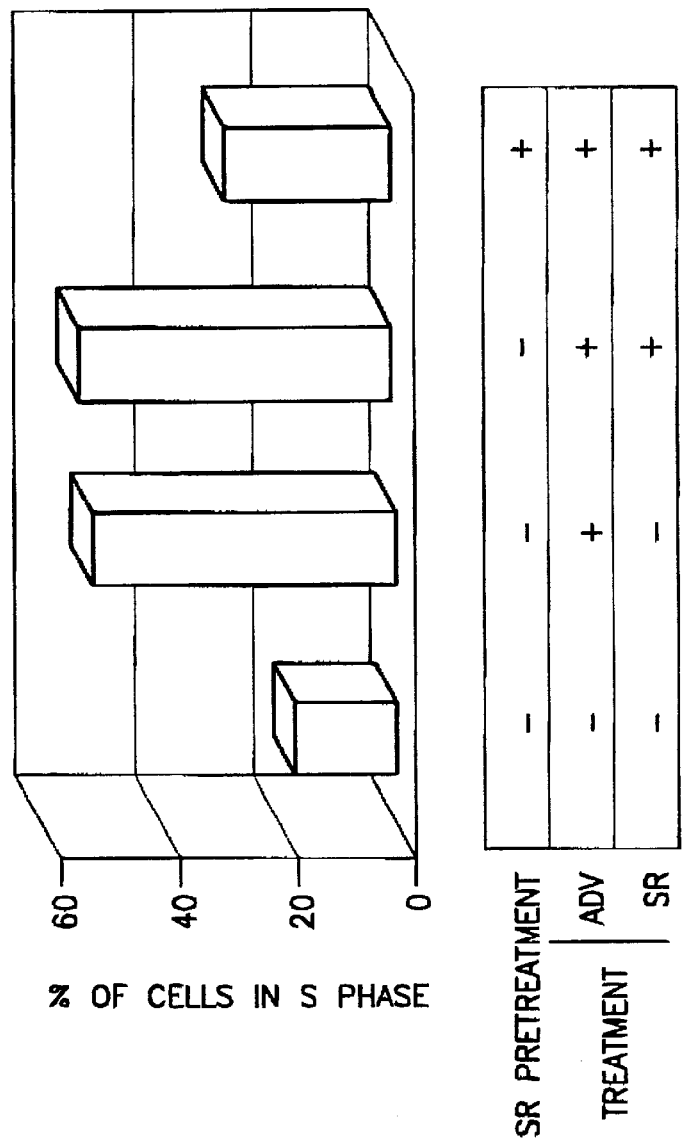
FIG. 3 depicts in vitro experimental data obtained in another assay conducted according to the present invention, showing the effects of Product R on the percentage of Hela cells in S phase.

FIG. 3 depicts the result of another experiment embodying the present invention. It shows that the pretreatment with Product R prior to adenovirus infection reduces the number of cells entering the S phase caused by the virus infection while post-infection treatment with Product R produces no significant effect in this regard.

While there have been shown, described and pointed out the features of the invention as applied to a preferred embodiment thereof, it will be understood that various omissions and substitutions and changes in the form and details of the devices illustrated, and in their operation, may be made by those skilled in the art without departing from the spirit of the invention. For example, the invention is not limited to the specific materials and equipment described in the foregoing embodiment. Similar materials from different sources or equivalent assay equipment may be satisfactorily used. It is expressly intended that all combinations of those elements and/or method steps which perform substantially the same function in substantially the same way to achieve the same results are within the scope of the invention.

The invention is not limited by the embodiments described above which are presented as examples only but can be modified in various ways within the scope of protection defined by the appended patent claims.

The following reference are incorporated herein by reference in their entirety.

REFERENCES

1. Sherr, C. J. Mannalian $G_1$. Cyclins. *Cell*, Vol. 73, 1059–1065, Jun. 18, 1993
2. Hunter, T. Braking the Cycle, *Cell* Vol. 75, 839–84 1, Dec. 3, 1993
3. *Science*, p. 1646, Dec. 10, 1993
4. Research News. How Cells Cycle Toward Cancer. *Science*. Vol. 263, 319–321, Jan. 21, 1994
5. Research News. How p53 Suppresses Cell Growth. Science. Vol. 262, 1644–1645, Dec. 10, 1993
6. Teodoro, J. G., Branton, P. E. Minireview. *J. of Virology*, March 1997, p. 1739–1746
7. Subramanian, T., B. Tarodi. Cell Growth Differ. 1995, 6:131–137
8. Teodoro, J. G. Oncogene, 1995, 11:467–474
9. Marcellus, R,C, *J. of Virology*, 1996, 70:6207–6215
10. Tollefson, A. E., J of Viology, 1996, 70:2295–2306

We claim:

1. A method of measuring effects of Product R on adenovirus infection of a cultured cell, comprising the steps of
   (a) culturing a cell in a container,
   (b) adding a predetermined amount of Product R in said container and culturing cells in said container,
   (c) infecting cells in said container with adenovirus,
   (d) culturing cells in said container, and
   (e) determining the percentage of cells in a particular cell cycle phase in said container.

2. The method of claim 1, wherein cells in said container are infected with 20 pfu/cell of adenovirus type 5 in step (c).

3. The method of claim 1, wherein cells in said container are cultured for one hour at 37° C. in 5% $CO_2$ in step (b), and cells in said container are cultured for 14 hours in DMEM supplemented with 5% fetal calf serum and 5% calf serum in step (d).

4. The method of claim 1, wherein the percentage of cells in a particular cell cycle phase in said container is determined by using a flow cytometry technique.

5. The method of claim 1, further comprising another step where DNA fragmentation analysis is performed on cells in said container at the completion of step (d).

6. The method of claim 1, further comprising another step where Western blotting is performed on cells in said container at the completion of step (d) to determine the amount of the p53 protein.

7. A method of measuring effects of Product R on virus infection of Hela cells, comprising the steps of
   (a) seeding Hela cells into a plurality of culture containers and growing said cells to confluence;
   (b) taking a first container prepared in step (a) and adding nothing to it so that it is suitable to be used as a control; taking a second and a third culture containers prepared in step (a), adding to both a predetermined amount of Product R followed by a period of incubation and then infecting the Hela cells in said third culture container with a virus; and taking a fourth and fifth culture containers prepared in step (a), affecting the Hela cells in both containers with said virus followed by a first period of incubation and then adding Product R into said fourth container followed by a second period of incubation;
   (c) culturing said first, second, third, fourth and fifth container prepared in step (b) for a period of time; and
   (d) performing one or more tests to determine the number of the Hela cells in a particular cell cycle phase in each of said first, second, third, fourth and fifth containers at the completion of step (c).

8. The method of claim 7, wherein the Hela cells in said third, fourth and fifth containers are infected with adenovirus type 5.

9. The method of claim 7, wherein said period of incubation for the second and third containers in step (b) is conducted for one hour at 37° C. in 5% $CO_2$; said first and second period incubations for said fourth and fifth containers in step (b) are each conducted for one hour at 37° C. in 5% $CO_2$; and said culturing in step (c) continues for 14 hours in DMEM supplemented with 5% fetal calf serum and 5% calf serum.

10. The method of claim 7, wherein step (d) is performed by using a flow cytometry technique.

11. The method of claim 7, further comprising another step where DNA fragmentation analysis is performed on Hela cells in each of said containers at the completion of step (c).

12. The method of claim 7, further comprising another step where Western blotting is performed on Hela cells in each of said containers at the completion of step (c) to determine the amount of the p53 protein.

* * * * *